United States Patent
Aksu et al.

(10) Patent No.: US 11,191,580 B2
(45) Date of Patent: Dec. 7, 2021

(54) IMPLANTATION AID FOR THE USE OF SURFACE-SENSITIVE IMPLANTS

(71) Applicant: KARL LEIBINGER MEDIZINTECHNIK GMBH & CO. KG, Mühlheim (DE)

(72) Inventors: Adem Aksu, Villingen-Schwenningen (DE); Frank Reinauer, Emmingen-Liptingen (DE); Tobias Wolfram, Dreieich (DE)

(73) Assignee: KARL LEIBINGER MEDIZINTECHIKGMBH & CO. KG, Muehlheim (DE)

( * ) Notice: Subject to any disclaimer, the term of this patent is extended or adjusted under 35 U.S.C. 154(b) by 0 days.

(21) Appl. No.: 16/311,190

(22) PCT Filed: Jul. 3, 2017

(86) PCT No.: PCT/EP2017/066479
§ 371 (c)(1),
(2) Date: Dec. 19, 2018

(87) PCT Pub. No.: WO2018/007308
PCT Pub. Date: Jan. 11, 2018

(65) Prior Publication Data
US 2019/0183550 A1    Jun. 20, 2019

(30) Foreign Application Priority Data
Jul. 4, 2016 (DE) .................. 10 2016 112 154.1

(51) Int. Cl.
*A61B 17/86* (2006.01)
*A61B 17/88* (2006.01)
*A61B 17/00* (2006.01)

(52) U.S. Cl.
CPC ........ *A61B 17/8615* (2013.01); *A61B 17/863* (2013.01); *A61B 17/864* (2013.01);
(Continued)

(58) Field of Classification Search
CPC ..... A61B 17/84; A61B 17/86; A61B 17/8605; A61B 17/861; A61B 17/8615;
(Continued)

(56) References Cited

U.S. PATENT DOCUMENTS 2,871,899 A * 2/1959 Coyle .................... B25G 1/105
                                                          81/177.1
4,269,246 A * 5/1981 Larson ............... A61B 17/8615
                                                          411/403
(Continued)

FOREIGN PATENT DOCUMENTS

CN      2756822 A2   7/2014
DE    202004004844 U1   5/2004
(Continued)

OTHER PUBLICATIONS

International Search Report and Written Opinion, PCT/EP2017/066479, dated Nov. 6, 2017 (in German) (10 pp.).
(Continued)

*Primary Examiner* — Andrew Yang
(74) *Attorney, Agent, or Firm* — Eversheds Sutherland (US) LLP (57) ABSTRACT

The present application relates to an implantation set including a tool or an aid, and at least one bone contact member adapted thereto, therefore a device designed for direct contact with a bone, the bone contact member having a greater hardness in a region intended for contact by the tool or aid than the tool or aid in a region intended for contact with the bone contact member.

18 Claims, 6 Drawing Sheets

(52) U.S. Cl.
CPC .......... *A61B 17/866* (2013.01); *A61B 17/888* (2013.01); *A61B 17/8888* (2013.01); *A61B 2017/0023* (2013.01); *A61B 2017/0046* (2013.01)

(58) Field of Classification Search
CPC ... A61B 17/863; A61B 17/864; A61B 17/866; A61B 17/88; A61B 17/8875; A61B 17/8877; A61B 17/888; A61B 17/8886; A61B 17/8888; B25B 15/001; F16B 23/00
See application file for complete search history.

(56) References Cited

U.S. PATENT DOCUMENTS

| | | | | |
|---|---|---|---|---|
| 5,019,080 | A * | 5/1991 | Hemer | A61B 17/8615 411/402 |
| 6,016,727 | A * | 1/2000 | Morgan | A61B 17/8615 411/403 |
| 6,330,845 | B1 | 12/2001 | Meulink | |
| 7,730,812 | B2 * | 6/2010 | Edland | F16B 23/003 81/460 |
| 9,078,740 | B2 * | 7/2015 | Steiner | A61B 17/8875 |
| 2002/0169453 | A1 | 11/2002 | Berger | |
| 2003/0054318 | A1 | 3/2003 | Gervais et al. | |
| 2004/0254576 | A1 | 12/2004 | Dunbar, Jr. et al. | |
| 2005/0216015 | A1 | 9/2005 | Kreidler | |
| 2011/0015682 | A1 | 1/2011 | Lewis et al. | |
| 2012/0109111 | A1 * | 5/2012 | Li | A61M 39/0247 604/543 |
| 2012/0109135 | A1 * | 5/2012 | Bailey | A61B 17/17 606/87 |
| 2012/0150237 | A1 | 6/2012 | Combrowski | |
| 2012/0312130 | A1 * | 12/2012 | Bauer | B25B 13/065 81/461 |
| 2013/0218214 | A1 | 8/2013 | Beyar et al. | |
| 2014/0018862 | A1 * | 1/2014 | Koay | A61B 17/8057 606/281 |
| 2014/0207233 | A1 | 7/2014 | Steiner et al. | |
| 2015/0173775 | A1 * | 6/2015 | Sweeney | A61B 17/164 606/80 |
| 2016/0221135 | A1 * | 8/2016 | Tiefenbock | B23B 51/00 |

FOREIGN PATENT DOCUMENTS

| | | |
|---|---|---|
| DE | 202011107522 U1 | 12/2011 |
| DE | 202013105409 U1 | 12/2013 |
| JP | 59-116170 U | 6/1984 |
| JP | 2009 008112 A2 | 1/2009 |
| WO | 2005053753 A2 | 6/2005 |
| WO | 2011080104 A1 | 7/2011 |

OTHER PUBLICATIONS

International Search Report, PCT/EP2017/066479, dated Nov. 6, 2017 (in English) (3 pp.).
German Office Action, GE 10 2016 112 154.1, dated Jan. 20, 2017 (with attached English Translation) (9 pp.).
Chinese Office Action for 201780039418.5, dated Mar. 3, 2021 (with English translation) (12 pp.).
JP Office Action for 2018-567710, dated May 25, 2021 (with English translation) (9 pp.).

* cited by examiner

IMPLANTATION AID FOR THE USE OF SURFACE-SENSITIVE IMPLANTS

TECHNICAL FIELD

The invention relates to an implantation set comprising a tool and at least one bone contact member adapted thereto, which is designed as a device for direct contact with a bone, in particular such a set which enables the insertion, removal and attachment of implants made of materials with sensitive surface modifications and/or coatings with no damage or as little damage as possible to the implant. This can be achieved, for example, with a medical tool/screw combination in which a screwdriver acts as a tool and which includes at least one screw which fits the screwdriver and is suitable for screwing into a bone of a mammal such as a human, for instance, the screw having a screw head on the one hand and a thread on the other hand, the screw head having a tool mounting which is adapted geometrically and in terms of surface topography to the outer contour of a tip of the screwdriver.

BACKGROUND OF THE INVENTION

Prior art screws and screwdrivers intended for use in medical technology are already known. Usually, however, the tools are harder than the screws. This has the negative effect that damage to the screw head can occur when the screw is screwed in, especially in the contact region with the tool. Near-surface damages to coated implants or surface-modified implants during attachment and insertion are also known and can ultimately lead to implant failure. In addition, problems may occur when removing implants, e.g. a screw, which is due to the previously inflicted damage. This can even be so severe that the screw must remain in the body even though this is not medically indicated. Examples of the prior art are known from DE 20 2013 105 409 U1, DE 20 2004 004 844 U1 and US 2011/0 015 682 A1.

In classical mechanical engineering, however, it is preferable to have a hard tool and to use a softer screw. This is due to the fact that in case of damage only the screw has to be replaced, but not the much more expensive tool.

SUMMARY OF THE INVENTION

It is the object of this invention, however, to provide a better solution, especially for the medical technology sector, which should make it possible to attach, insert and remove innovative implants made of new materials with special surface coatings and modifications, which has become necessary in recent times, without damaging the implant itself. The loosening of screws and screwing them in again after a loosening process is also to be facilitated with the help of the instruments and tools mentioned.

This object is solved surprisingly simply by the invention in that the bone contact member has a greater hardness in a region intended for contact by the tool than the tool in a region for contact with the bone contact member.

When implementing a screwdriver-screw-type solution, the object is achieved in that the screw head at least in the region of the tool mount has a greater hardness than at least that part of the tip of the screwdriver which is intended for contacting the tool mount. In contrast to what has previously been taught in any textbook for an engineer, the exact opposite is now the case and the basically much softer screw is made harder than the screwdriver. What is reprehensible in the normal mechanical engineering sector, however, is suitable in the medical technology sector, especially with the problems that exist there. The generally low hardness of the implants (including screws) is due to the materials used and the surface changes. They have better properties with regard to medically/biologically relevant aspects, but are mechanically characterized by a loss of hardness in comparison to the traditionally uncoated implants made of titanium or stainless steel.

Thus, a solution is presented that is adequate for the medical technology sector and yet easy to implement. It offers invaluable advantages, especially in the case of auxiliaries, tools and structured devices for the insertion, attachment and fixation of implants made in particular of biodegradable metals and their alloys as well as resorbable or non-absorbable polymers, ceramics and their composites. In addition, this offers solutions for the field of classic materials for implants, such as titanium or stainless steel, whose surfaces have been mechanically, chemically or physically optimized and structured, but where significantly more sensitive surfaces have been created. This results in solutions especially for implantation aids, which are intended for the attachment, insertion and removal of implants (e.g. a screw or plate) made of biodegradable or non-biodegradable metals and alloys as well as resorbable or non-resorbable polymers, ceramics and their composites.

Advantageous embodiments are claimed in the subclaims and are explained in more detail below.

For example, it is advantageous if the tool mount is designed as a recess, since the screwdriver can then simply penetrate into the recess with its tip and—even with a slight angular offset of the longitudinal axis of the screwdriver relative to the longitudinal axis of the screw, e.g. by up to approx. 15° to approx. 20°—the screw can still be tightened without destroying the tool mount.

In order to keep the production cost-efficient and universally applicable, it is best practice if the tool mount has a slot or a cross slot or an Allen key or a Torx geometry and the screwdriver at the tip is formed to be congruent/matching thereto.

In order to produce a self-holding effect, it is advantageous if the tool mount, which is designed as a recess, has screwdriver tip contact surfaces (exactly) aligned in the longitudinal direction of the screw, whereas the tool mount contact surfaces at the tip of the screwdriver are inclined (diagonally/transversely/set at an angle) relative to the longitudinal direction of the screw (and/or screwdriver).

A self-holding effect can be achieved particularly well if all tool mount contact surfaces of the screwdriver intended for contacting the screwdriver tip contact surfaces of the screw are inclined between approx. 2.5° to approx. 7.5° to the longitudinal axis of the screwdriver or to its axis of rotation, preferably by approx. 5°+/−0.25°.

An advantageous exemplary embodiment is also characterized in that the geometries and the dimensions of the recess in the screw head of the tip, designed as a projection, of the screwdriver are adapted to each other in such a way that the screw is forced to hold itself on the tip when the tip engages the recess, for example by creating a (press) fit.

In order to use the threading effect of a wire, it is advantageous if the screw and the screwdriver each have a preferably centrally arranged through-hole. This means that both the screw and the screwdriver contain one through-hole each. A wire can then simply be put into the patient's bone, a drill pushed over the wire can then drill into the bone around the wire, and then, especially after removing the drill, a screw guided over the wire can be further screwed into the bone using a screwdriver also guided by the wire. Of course, the wire can also be removed after drilling or after inserting the screw into the hole.

It is useful if the through-holes of screw and screwdriver are circular in cross-section and have the same size in the mutual contact region. This prevents the wire from getting caught. The guidance is improved.

In order to be able to fall back on conventional wire configurations and to enable good cleaning of the screwdriver, it is advantageous if the through-hole in the screwdriver is designed so as to be stepped several times, for instance twice or three times, with a smallest diameter being approx. 0.6 mm, an average diameter approx. 0.8 mm and a larger diameter approx. 1.0 mm.

It is advantageous if a step of the through-hole of the screwdriver is present in a shaft region extending from a grip region to the tip, preferably in the anterior, distal third of the shaft.

It is also advantageous if the screwdriver is designed as an integral, single-material component, e.g. made of plastic, for instance injection-molded plastic material, a metal such as an iron, light metal or titanium alloy, or if the screwdriver is constructed in several parts and/or in several materials. Particularly in the latter case, it is easy to replace individual components of the screwdriver, making cleaning and repair easier.

Especially in the case of a multi-part and/or multi-material design, it is advantageous if the handle is made of plastic, such as silicone or an injection-molded material, the shaft is made of metal, such as iron or light metal or titanium and/or the tip comprises or is made of plastic, such as a polymer or a fiber-reinforced plastic or light metal or ceramic, or the tip has a ceramic coating on the outside.

If the tip is exchangeably coupled to the handle, for example by means of the shaft, maintenance can be limited to the component interacting with the screw.

It is advantageous if the screwdriver is designed as a torque wrench, as this effectively prevents the screw from being overtightened.

The screw may also be made from coated material or comprise coated metal, e.g. a ceramic coating. Furthermore, other implants, such as plates, "meshes" or "scaffolds", also have coatings. These coatings or surface modifications are often damaged when the implants are fitted (attached) or inserted, so that unspecific reactions can occur in the damaged regions during the interaction of the implant surface with tissues, such as chemical corrosion, material degradation or chemical degradation. This is to be prevented by the changes mentioned for all instruments that come into direct contact with the implants during attachment, insertion and removal.

It has proven to be successful if the screw and/or the tip of the screwdriver is coated by means of PVD or CVD. In addition, the tools and instruments can also be specifically modified on the surface, e.g. a roughness in the micrometer range can be used to give subsequent polymeric surface protection layers improved adhesion to the surface so that this layer is soft but remains stably on the instrument, e.g. the screwdriver or the mounting tool. With these modified instruments/tools, a topography in the micrometer range is first applied by physical, chemical or mechanical processes such as pickling, abrasive water blasting, sand blasting or particle deposits. The polymers that form the surface layer can then be applied. These can be silicone-based polymers, for example, but also polyurethanes such as Teflon, polypropylene, PEEK, PEAK, HDPE, LDPE, UHMWPE or polyamides. These can be easily applied e.g. by chemical coating processes. The polymers can also be subsequently cross-linked (chemical cross-linking) to prevent mechanical abrasion during fitting and insertion.

Another possibility is the polymer-based bonding of the screw head and screwdriver. Here, the implant is directly connected to the screw blade by polymeric, bio-resorbable chemical substances such as PDLLA, PCL, PLGA, PLA and PGA and inserted without any further mounting. The screw blade and any implants are then separated either mechanically or thermally so that the implant can remain in the body and the part of the instrument, e.g. the screw blade, can be discarded. This ensures that there is no direct mechanical interaction between the tool/instrument and the implant.

If the set contains a preferably biodegradable and/or metallic implant to be fastened by the screw, a single case-related packing unit can be used to effect a targeted care of the patient for the operation.

Standardized systems with blades and inserts with known interfaces, such as Torx, cross slot, internal polygon and (single) slot, can be significantly improved. The interface may consist of different polymers or a single polymer. The interface may have different ceramics or different composite materials. Fiber-reinforced materials are particularly suitable for the interface.

The interface can be improved if it is made from different materials listed above in combination with a coating or coatings or surface modifications. In particular, the use of an inherent two- or three-dimensional hollow structure is a viable option. It is possible to make use of the self-retaining function of the connecting element. It is also possible to ensure a tightening or untightening torque, e.g. by configuring the screwdriver as a torque wrench.

The interface may be equipped with or without a function to easily accommodate an implant consisting of biodegradable metallic, resorbable or non-absorbable polymers, ceramics and their composites. A function for easy removal from the packaging may be provided. Furthermore, interfaces may be provided with or without a function for specific energy transfer between the aid, tool or structured device and the specific mounting or biodegradable metallic implant itself. An angle-independent alignment using special geometries is possible. Finally, a biodegradable metallic implant can be fixed with minimal time and effort.

For the tips of the screwdriver, which can also be referred to as blades, the following materials have proven themselves. Polymers, in particular with a Rockwell hardness (according to ISO-standard 2039-2) between R30 to R125, M50 to M200, E50 to E200. This polymer may also have a Shore hardness from 20 Shore A to 100 Shore A, 20 Shore B to 100 Shore B, 20 Shore C to 100 Shore C, 20 Shore D to 100 Shore D. If a ceramic is used in this region, a Vickers hardness of 800 to 2000 should be available. For fiber-reinforced materials in this range, a Rockwell hardness, see ISO-standard 2039-2, should be set from R30 to R150 or M50 to M250 or E50 to E250, respectively.

The materials listed above can also be used in combination with one or more coatings and/or one or more surface modifications. In the case of polymers, a Rockwell hardness in accordance with the ISO-standard 2039-2 from R30 to R200 or M50 to M300 or E50 to E300 should then be available, or according to the Shore scale from 20 Shore A to 200 Shore A, 20 Shore B to 200 Shore B, 20 Shore C to 200 Shore C or 20 Shore D to 200 Shore D. For ceramics, the Vickers hardness should range from approx. 800 to approx. 3000. For fiber-reinforced materials according to Rockwell, see ISO-standard 2039-2, a hardness from R30 to R150 or M50 to M250 or E50 to E250 should be set. For metals (alloyed and unalloyed) there are conversion tables according to DIN standard 50150. See, for instance in the Internet under http://www.chemie.de/lexikon/H%c3%a4rte.html#h.c3.a4rtepr.c3.bcfung na ch Rockwell.

BRIEF DESCRIPTION OF THE DRAWINGS

The invention is explained in more detail below using a drawing. Several exemplary embodiments are shown in more detail, which can be modified. In the Figures.

DETAILED DESCRIPTION

The Figures are only schematic in nature and only serve to understand the invention. Identical elements are provided with the same reference signs. The characteristics of the individual exemplary embodiments can also be exchanged with each other.

Figure 1:
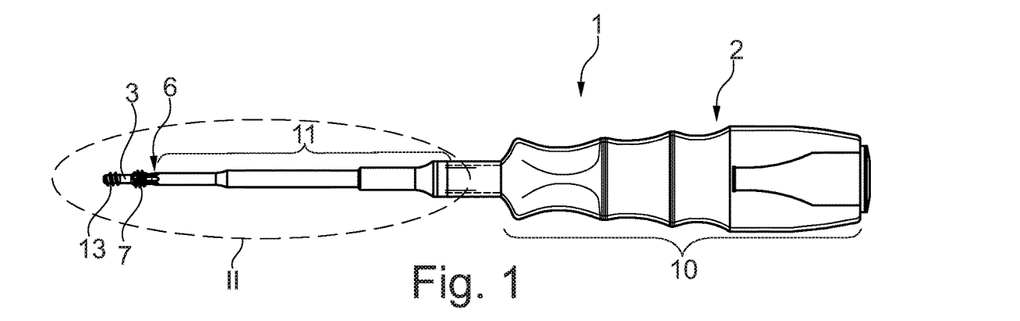
FIG. 1 shows an implantation set according to the invention in a side view with a screwdriver placed on a screw with its tip.

FIG. 1 shows a first implantation set 1 according to the invention. This has a screwdriver 2. The screwdriver 2 contacts a (bone) screw 3. The screw 3 is intended for screwing into a bone 4, see FIG. 12, and then serves to fasten an implant 5 to the bone 4.

Coming back to FIG. 1, attention is drawn to a tip 6 of the screwdriver 2. This tip 6 engages in a torque-transmitting state in a tool mount 8 of screw 3, namely at an end at the screw head side. The tool mount 8 of screw 3 is designed as a recess 9. The interaction of tip 6 and recess 9 becomes obvious when looking at FIGS. 6 and 8.

Coming back to FIG. 1, it is noticeable that a shaft 11 is interposed between the distally ending tip 6 and a handle/grip region 10 of the screwdriver. The shaft 11 has outer steps 12. There are three outer steps 12.

Figure 2:
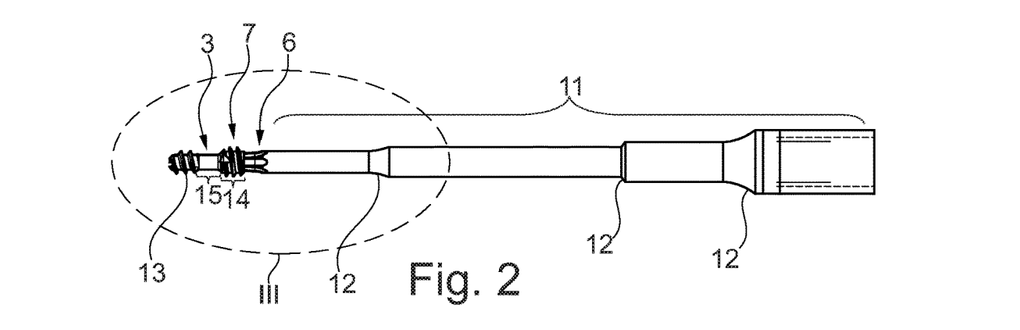
FIG. 2 shows an enlargement of area II from FIG. 1.
Figure 3:
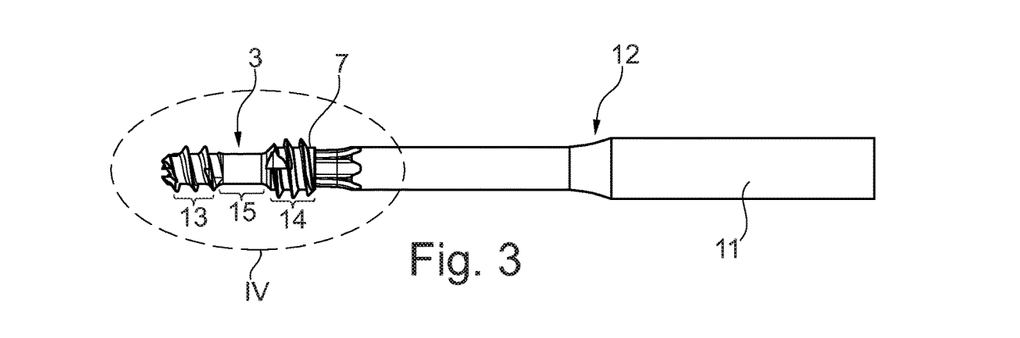
FIG. 3 shows an enlargement of area III from FIG. 2.
Figure 4:
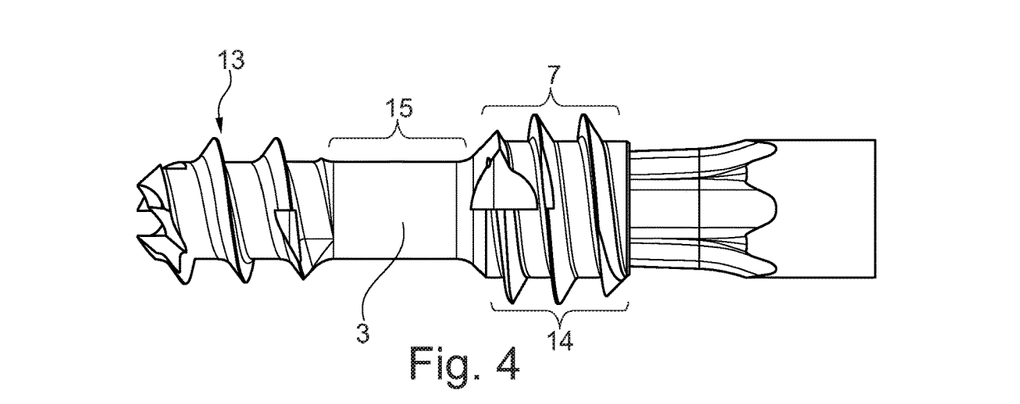
FIG. 4 shows an enlargement of area IV from FIG. 3.

A bone thread/external thread 13 is present at the end of screw 3 remote from the screw head. An implant contact (external) thread 14 is provided in the screw head region. It may have the same or a different pitch than the bone thread/external thread 13. There is a thread-free region 15 between the bone thread/external thread 13 and the implant contact thread 14 on the outside. This can be seen particularly clearly in FIGS. 2 to 4.

Figure 5:
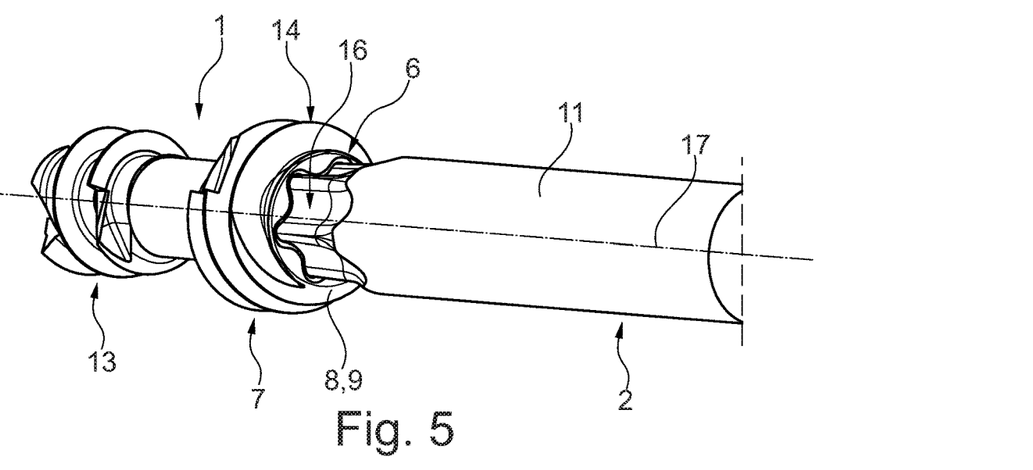
FIG. 5 is a perspective representation of the area shown in FIG. 4.

FIG. 5 shows the penetration of the tip 6 of the screwdriver 2 with a regular eightfold Torx configuration on the outside in a matching recess 9 of the tool mount 8 in the screw head 7 of screw 3.

Figure 6:
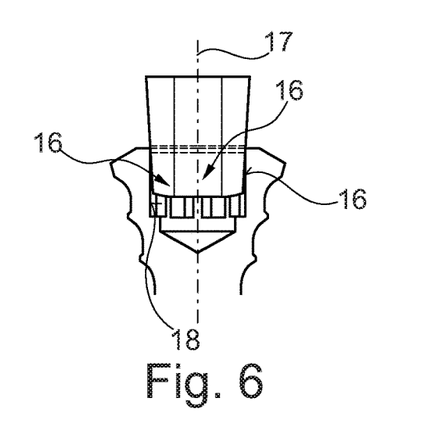
FIG. 6 shows a coupling region between the screwdriver and the screw partially shown in longitudinal section.

FIG. 6 shows that the tip 6 of the screwdriver 2 has tool mount contact surfaces 16. These tool mount contact surfaces 16 are inclined relative to a longitudinal axis 17 of the screwdriver 2 or the screw 3. An angle α appears. A particularly preferred value for α is 5°, in order to achieve a self-retaining effect with the Torx insert shown. The tool mount contact surfaces 16 make contact with screwdriver tip contact surfaces 18 in the screw 3.

Figure 7:
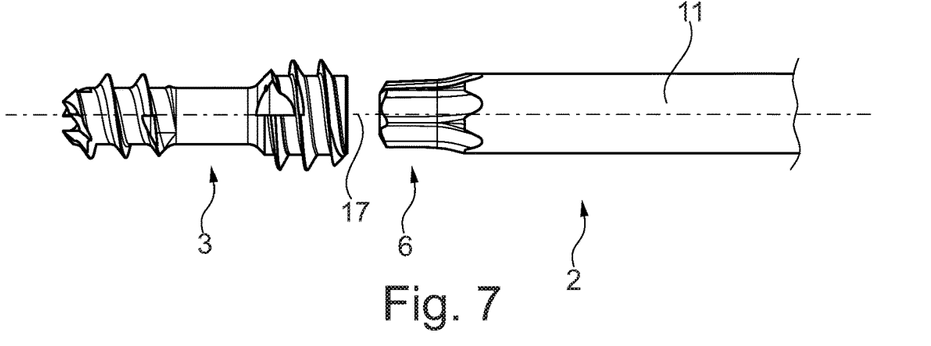
FIG. 7 is a perspective view of the screw and of the screwdriver shown only in the area of the tip/blade of the screwdriver, in a side view.
Figure 8:
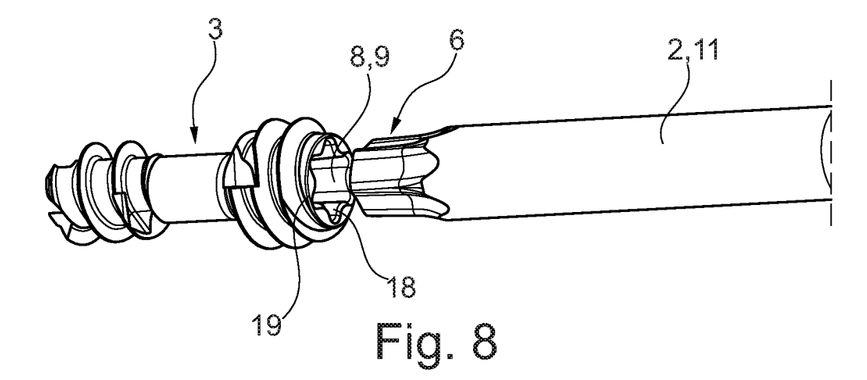
FIG. 8 shows the components from FIG. 7 in a perspective view.
Figure 9:
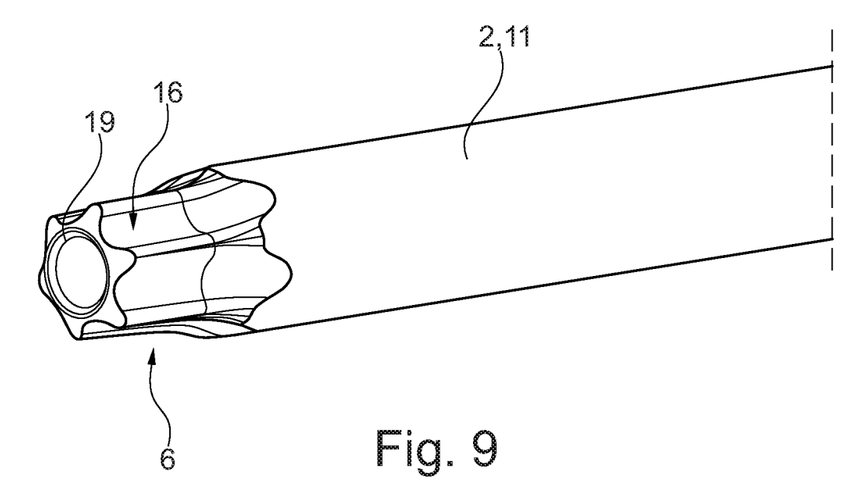
FIG. 9 is a perspective view distal to the tip of the screwdriver.

In FIGS. 7 and 8, the screw 3 is shown shortly before being contacted by the tip 6. As can be seen in FIG. 8 and especially in FIG. 9, both the screw 3 and the screwdriver 2 have a through-hole 19.

Figure 10:
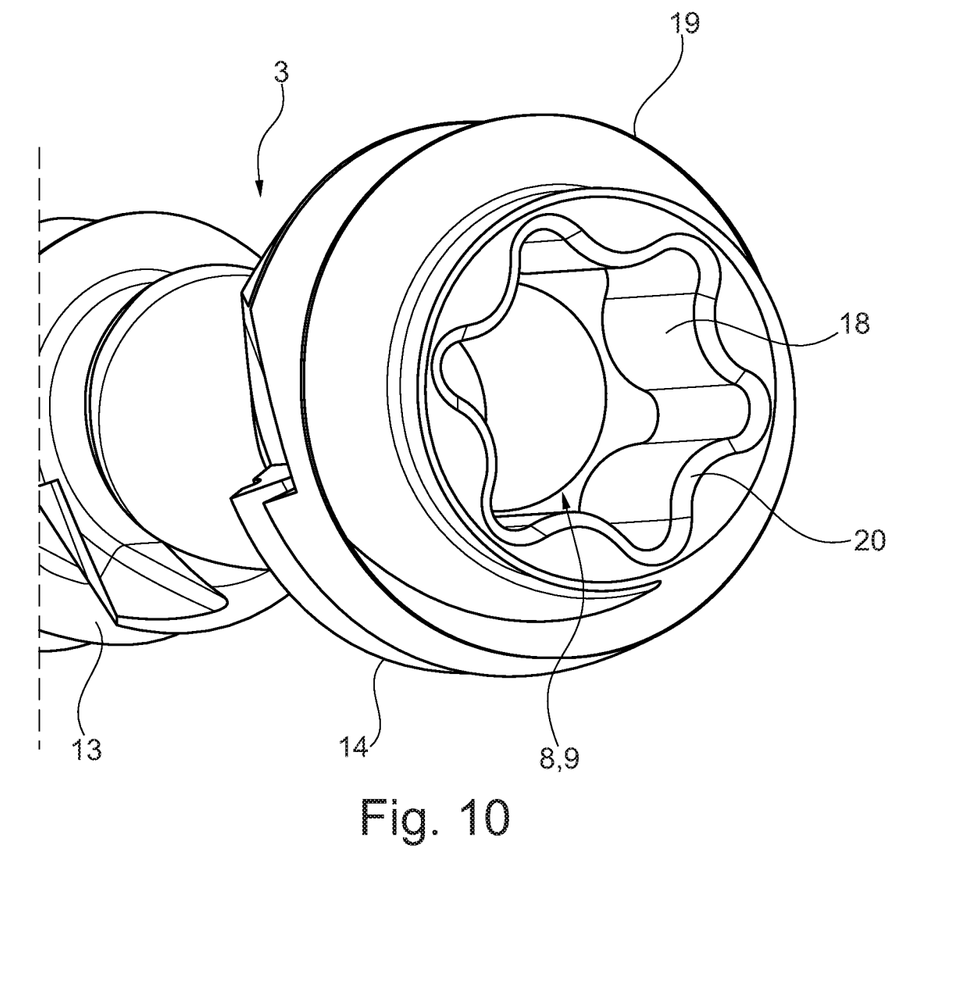
FIG. 10 is a perspective view of the screw head region with its tool mount provided there in the form of a Torx recess to realize a screw drive.

On the screw side, there is a chamfer 20 at the entrance of the recess 9. This can be clearly seen in FIG. 10.

Figure 11:
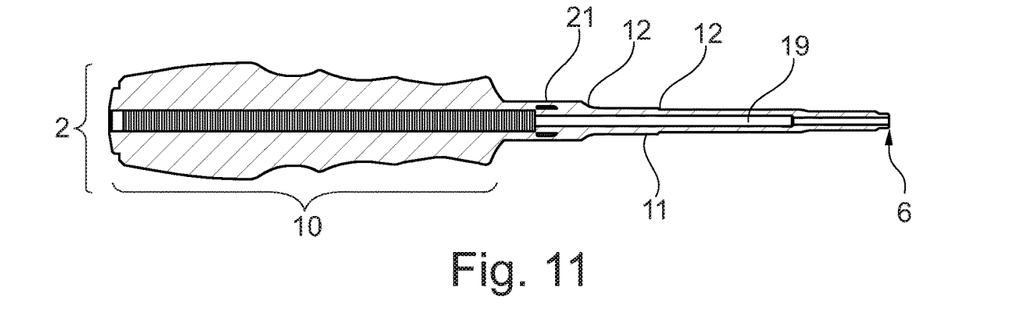
FIG. 11 shows a longitudinal section through the screwdriver of the implantation set from FIG. 1 to realize a two- or three-dimensional hollow structure.

The fact that the screwdriver 2 has several steps 21 in the through-hole 19 can be seen particularly well in FIG. 11. The handle 10 is a disposable article made of an injection-molded plastic material, whereas the shank 11 may be made from hardened steel if, for example, the screw is made of titanium. The screw 3 may also have a ceramic coating. The tip 6 can be made of a softer material and may be attached to the shaft 11 in connectable fashion. The fact that the through-hole 10 in the region of the handle 10 is larger than in the region of the tip 6 results in a good cleaning effect if, instead of using the handle 10 as a disposable item, it is to be reused and must therefore be cleaned.

Figure 12:
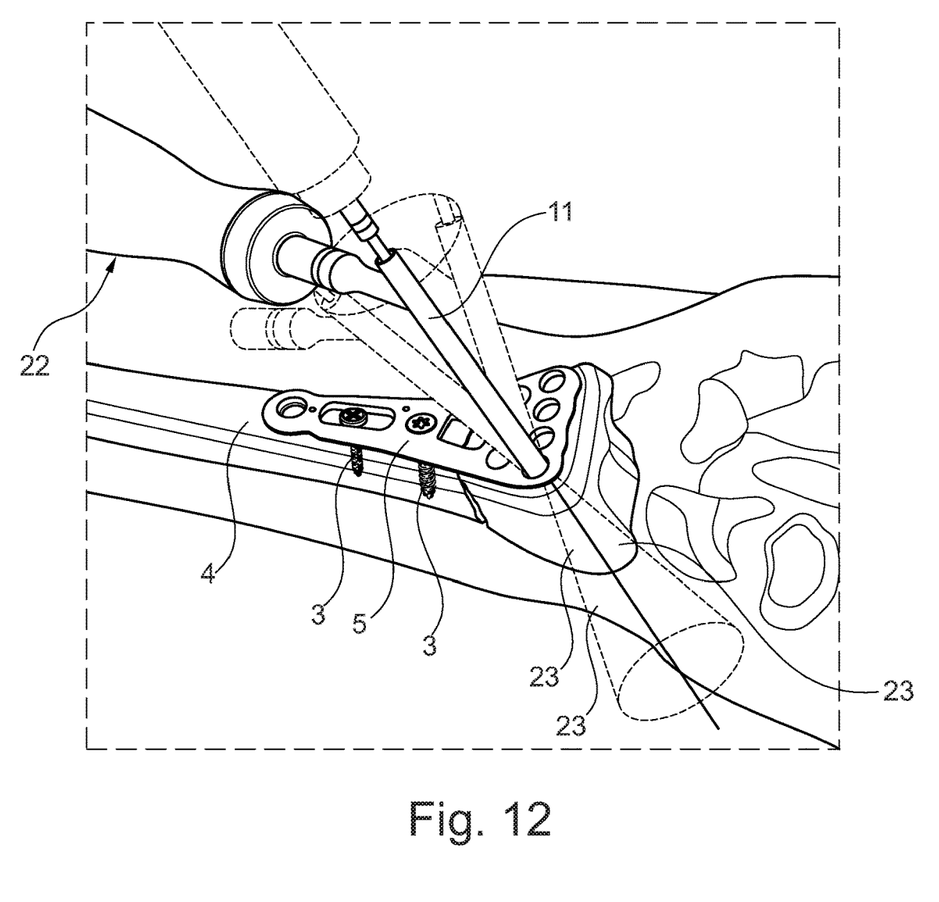
FIG. 12 shows the surgical use of the implantation set together with a biodegradable metallic implant with angle-independent alignment.

An angle-independent use of a tool is indicated in FIG. 12. However, a drilling tool 22 with a drill 23 is used there. Different positions of the drilling tool 22 and the drill 23 are indicated. Instead of the drilling tool 22, the screwdriver can be used with similar or identical angles/positions.

Figure 13:
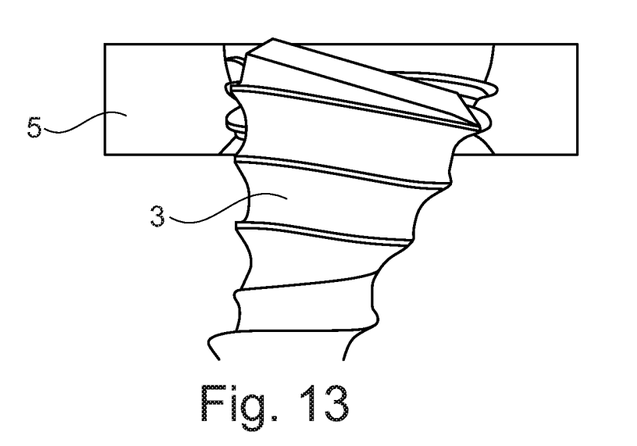
FIG. 13 shows an enlargement of a wedging region of the screw with the implant.
Figure 14:
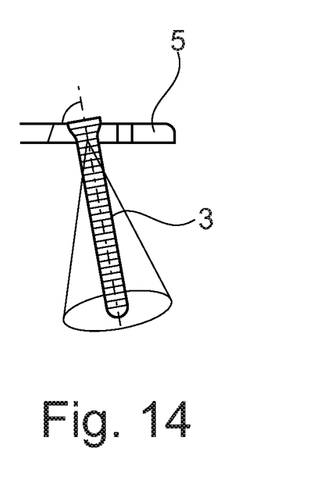
FIG. 14 is a side view to symbolize an angular offset of +/−approx. 15°, within which a wedging of the external thread of the screw with an internal thread of the implant is achieved.

The combination of the implant 5 and the (bone) screw 3 can easily be seen in FIG. 13, as well as in FIG. 14. However, the screw 3 has a slightly different design than the screw 3 used in the above examples.

The hardness for a screw 3 according to Brinell may have values from 70 to 90. The tip 6, which can also be referred to as a blade or blade tip, can also be manufactured as a disposable article, especially made of polymer, and should then have a hardness, e.g. using PEEK 1000, of M105 according to ISO 2039-2 or using PEEK with carbon fibers of M105 according to DIN ISO 2039-2. When using ceramics, a high hardness should prevail. Zirconium oxide or aluminum oxide is an alternative or additional material. Surface modifications such as oxidations, nitrifications and PVD coatings are conceivable. A self-retaining angle of approx. 5° on each side to the longitudinal axis (e.g. when using Torx) is conceivable, or an angle of 1° measured on each side or of 5° measured on each side. This results in sum angles of 5° or 2 to 10°.

It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

LIST OR REFERENCE NUMERALS 1 implantation set
2 screwdriver
3 (bone) screw
4 bone
5 implant
6 tip
7 screw head
8 tool mount
9 recess
10 handle/grip region
11 shaft
12 outer step
13 bone thread/external thread
14 implant contact thread
15 unthreaded region
16 tool mount contact surface of the tip of the screwdriver
17 longitudinal axis
18 screwdriver tip contact surface of the screw head of the screw
19 through-hole
20 chamfer
21 step
22 drilling tool
23 drill

We claim:

1. A medical implantation set comprising a tool and at least one bone contact member which is adapted thereto and is designed as a device for direct contact with a bone, wherein the bone contact member has a greater surface hardness in a region intended for contact by the tool than the tool in a region intended for contact with the bone contact member, wherein the tool is designed as a screwdriver and the bone contact member is designed as a screw forming an implant and matching the bone contact member for screwing into a bone, wherein the screw has a screw head and a thread, wherein the screw head has a tool mount which is geometrically adapted to an outer contour of a tip of the screwdriver, wherein the screw head has a greater hardness at least in a region of the tool mount than at least a part of the tip of the screwdriver provided for contacting the tool mount, and wherein the tool mount has screwdriver tip contact surfaces aligned in a longitudinal direction of the screw, whereas tool mount contact surfaces at the tip of the screwdriver are aligned so as to be inclined between approximately 2.5° to approximately 7.5° relative to the longitudinal direction of the screw.

2. The implantation set according to claim 1, characterized in that the tool mount is designed as a recess and/or the tool mount has a slot, cross-slot, hexagonal or Torx geometry and the screwdriver at the tip has a matching design.

3. The implantation set according to claim 2, characterized in that geometries and dimensions of the recess in the screw head and the tip of the screwdriver, which is designed as a projection, are adapted to one another such that a self-retaining effect of the screw on the tip is enforced when the tip engages in the recess.

4. The implantation set according to claim 1, characterized in that the screw and the screwdriver each have a through-hole.

5. The implantation set according to claim 4, characterized in that the through-holes of the screw and the screwdriver are of circular cross-section and have a same size in a mutual contact region.

6. The implantation set according to claim 4, characterized in that the through-hole in the screwdriver has a multi-step design.

7. The implantation set according to claim 1, characterized in that the tip of the screwdriver comprises a polymer with a Rockwell hardness of R30 to R125, M50 to M200, or E50 to E200.

8. The implantation set according to claim 1, characterized in that the tip of the screwdriver comprises a polymer with a Shore hardness of 20 Shore A to 100 Shore A, 20 Shore B to 100 Shore B, 20 Shore C to 100 Shore C, or 20 Shore D to 100 Shore D.

9. The implantation set according to claim 1, characterized in that the tip of the screwdriver comprises a ceramic with a Vickers hardness of 800 to 2000.

10. The implantation set according to claim 1, characterized in that the tip of the screwdriver comprises a fiber-reinforced material with a Rockwell hardness of R30 to R150, M50 to M250, or E50 to E250.

11. The implantation set according to claim 1, characterized in that the tip of the screwdriver comprises a polymer with a coating or a surface modification having a Rockwell hardness of R30 to R200, M50 to M300, or E50 to E300.

12. The implantation set according to claim 1, characterized in that the tip of the screwdriver comprises a polymer with a coating or a surface modification having a Shore hardness of 20 Shore A to 200 Shore A, 20 Shore B to 200 Shore B, 20 Shore C to 200 Shore C, or 20 Shore D to 200 Shore D.

13. The implantation set according to claim 1, characterized in that the tip of the screwdriver comprises a ceramic with a coating or a surface modification having a Vickers hardness of 800 to 3000.

14. The implantation set according to claim 1, characterized in that the tip of the screwdriver comprises a fiber-reinforced material with a coating or a surface modification having a Rockwell hardness of R30 to R150, M50 to M250, or E50 to E250.

15. The implantation set according to claim 1, characterized in that the screw has a Brinell hardness of 70 to 90.

16. The implantation set according to claim 1, wherein each of the tool mount contact surfaces are inclined between approximately 2.5° to approximately 7.5° relative to the longitudinal direction of the screw.

17. A medical implantation set for direct contact with a bone, comprising:
   a screwdriver; and
   at least one screw for screwing into the bone;
   wherein the screw comprises a tool mount which is geometrically adapted to an outer contour of a tip of the screwdriver;
   wherein the screw has a greater hardness at least in a region of the tool mount than at least a part of the tip of the screwdriver provided for contacting the tool mount; and
   wherein the tool mount comprises tool mount contact surfaces at the tip of the screwdriver inclined between approximately 2.5° to approximately 7.5° relative to the longitudinal direction of the screw.

18. The medical implantation set of claim 17, wherein each of the tool mount contact surfaces are inclined between approximately 2.5° to approximately 7.5° relative to the longitudinal direction of the screw.

* * * * *